United States Patent
Wang et al.

(10) Patent No.: US 10,183,132 B2
(45) Date of Patent: Jan. 22, 2019

(54) METHODS AND DEVICES FOR CO-DELIVERY OF LIQUID AND POWDERED HEMOSTATS AND SEALANTS

(71) Applicant: Ethicon, Inc., Somerville, NJ (US)

(72) Inventors: Yi-Lan Wang, Somerset, NJ (US); Leo B. Kriksunov, Ithaca, NY (US)

(73) Assignee: Ethicon LLC, Guaynabo, PR (US)

( * ) Notice: Subject to any disclaimer, the term of this patent is extended or adjusted under 35 U.S.C. 154(b) by 601 days.

(21) Appl. No.: 14/723,796

(22) Filed: May 28, 2015

(65) Prior Publication Data
US 2016/0074602 A1    Mar. 17, 2016

Related U.S. Application Data

(60) Provisional application No. 62/048,883, filed on Sep. 11, 2014.

(51) Int. Cl.
*A61M 15/00* (2006.01)
*A61M 11/00* (2006.01)
(Continued)

(52) U.S. Cl.
CPC ... *A61M 15/0003* (2014.02); *A61B 17/00491* (2013.01); *A61M 5/3137* (2013.01);
(Continued)

(58) Field of Classification Search
CPC .... A61B 17/00491; A61B 2017/00495; A61B 2017/00522; A61M 11/007; A61M 15/0003; A61M 2005/31598; A61M 2202/064; A61M 5/3137; A61M 5/31596; A61M 5/48
See application file for complete search history.

(56) References Cited

U.S. PATENT DOCUMENTS 369,767 A    9/1887  Beall
3,844,284 A  10/1974 Schoenfeld et al.
(Continued)

FOREIGN PATENT DOCUMENTS

CN    201346338    11/2009
JP    9182786 A     7/1997
(Continued)

OTHER PUBLICATIONS

International Search Report re: PCT/US2015/046520 dated Nov. 27, 2015.

*Primary Examiner* — Brandy S Lee
(74) *Attorney, Agent, or Firm* — David R. Crichton; Leo B. Kriksunov

(57) ABSTRACT

The present invention is directed to an integrated delivery device that is operable with one hand and provides co-delivery of a liquid medicant and a powder medicant onto a tissue or wound from a liquid medicant expression subunit and a powder medicant expression subunit. Each expression subunit having an actuator for the liquid medicant and the powder medicant contained therein that are positioned in close proximity to one other at a proximate end of said expression subunits and delivery cannulas for each of said expression subunits that positioned in close proximity to one other at a distal end of said expression subunits. The present invention also relates to method for using such integrated devices.

16 Claims, 7 Drawing Sheets

(51) Int. Cl.
*A61M 5/31* (2006.01)
*A61M 5/315* (2006.01)
*A61M 5/48* (2006.01)
*A61B 17/00* (2006.01)

(52) U.S. Cl.
CPC .......... *A61M 5/31596* (2013.01); *A61M 5/48* (2013.01); *A61M 11/007* (2014.02); *A61B 2017/00495* (2013.01); *A61B 2017/00522* (2013.01); *A61M 2005/31598* (2013.01); *A61M 2202/064* (2013.01)

(56) References Cited

U.S. PATENT DOCUMENTS

| | | | |
|---|---|---|---|
| 4,411,656 | A | 10/1983 | Cornett |
| 4,723,691 | A | 2/1988 | Minkevitch et al. |
| 5,957,340 | A | 9/1999 | Sawicki |
| 6,458,095 | B1 | 10/2002 | Wirt et al. |
| 6,699,229 | B2 | 3/2004 | Zinger et al. |
| 6,743,248 | B2 * | 6/2004 | Edwards .......... A61B 17/00491 606/214 |
| 7,923,031 | B2 | 4/2011 | Moller |
| 7,946,417 | B2 | 5/2011 | Plishka et al. |
| 7,951,108 | B2 | 5/2011 | Harper et al. |
| 7,967,779 | B2 | 6/2011 | Bertron et al. |
| 8,056,762 | B2 | 11/2011 | Wright et al. |
| 8,376,989 | B2 | 2/2013 | Rissman et al. |
| 2003/0040701 | A1 | 2/2003 | Dalmose |
| 2003/0187408 | A1 | 10/2003 | Marx |
| 2006/0100664 | A1 * | 5/2006 | Pai .................... A61B 17/00491 606/214 |
| 2010/0219200 | A1 | 9/2010 | Plishka et al. |
| 2010/0249829 | A1 * | 9/2010 | Rissman .......... A61B 17/00491 606/213 |
| 2010/0305548 | A1 * | 12/2010 | Kraushaar ............. A61J 1/2096 604/518 |
| 2011/0021982 | A1 | 1/2011 | Keller |
| 2011/0066182 | A1 * | 3/2011 | Falus .................. A61L 24/0031 606/214 |
| 2011/0178495 | A1 | 7/2011 | Ji |
| 2011/0245866 | A1 * | 10/2011 | Cassingham .... A61B 17/00491 606/213 |
| 2012/0108509 | A1 * | 5/2012 | Hissong ................ A61L 24/043 514/7.6 |
| 2013/0316974 | A1 | 11/2013 | Wang et al. |
| 2014/0005636 | A1 | 1/2014 | Wang et al. |

FOREIGN PATENT DOCUMENTS

| | | |
|---|---|---|
| WO | WO 2005/030111 | 4/2005 |
| WO | WO 2013/183476 | 12/2013 |

\* cited by examiner

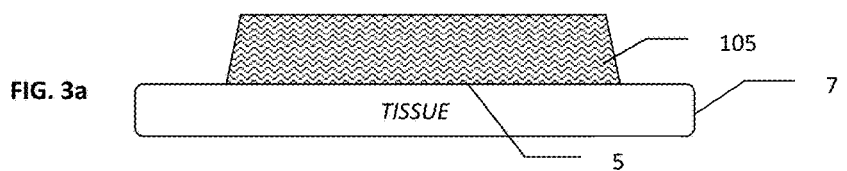
FIG. 3a
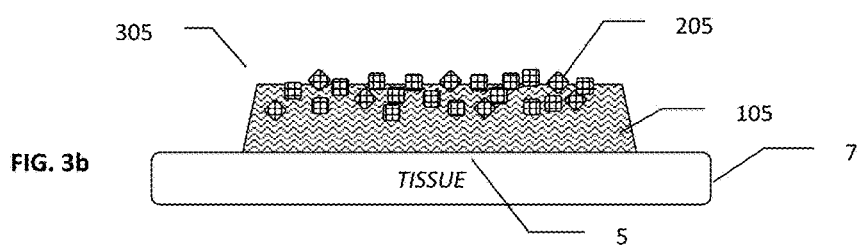
FIG. 3b
FIG. 4
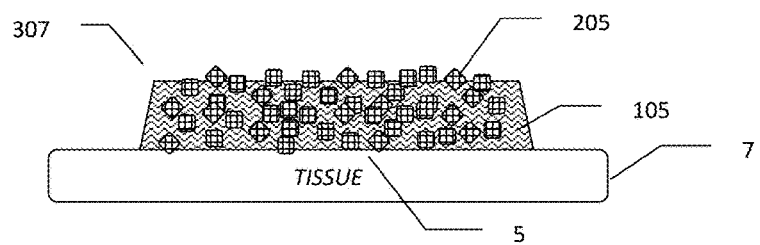
FIG. 5
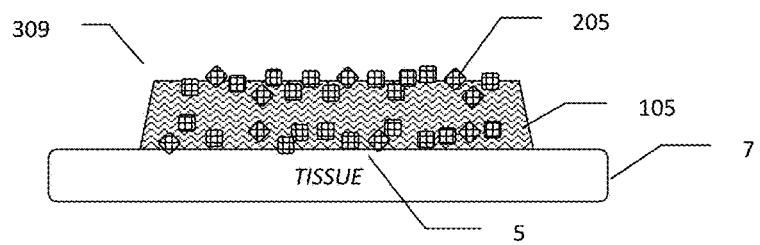

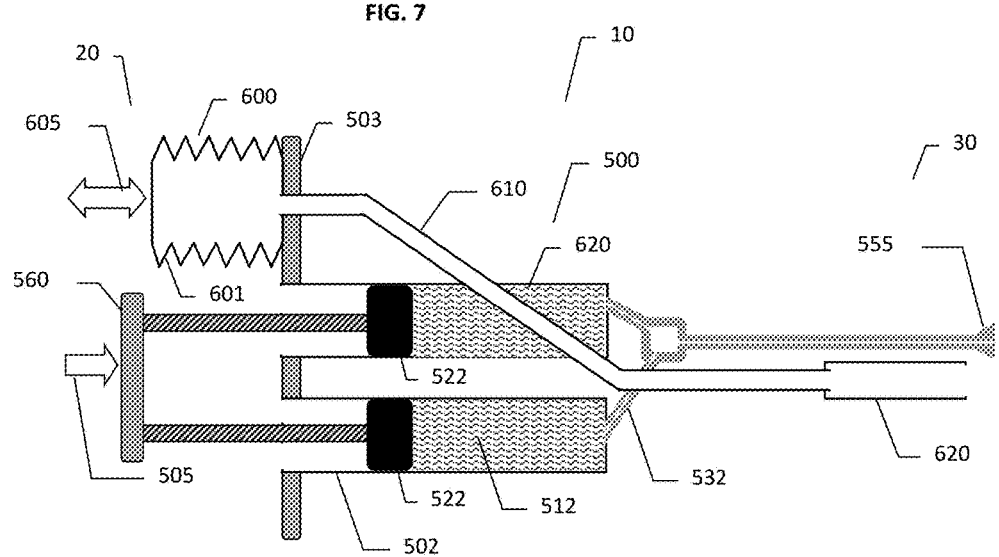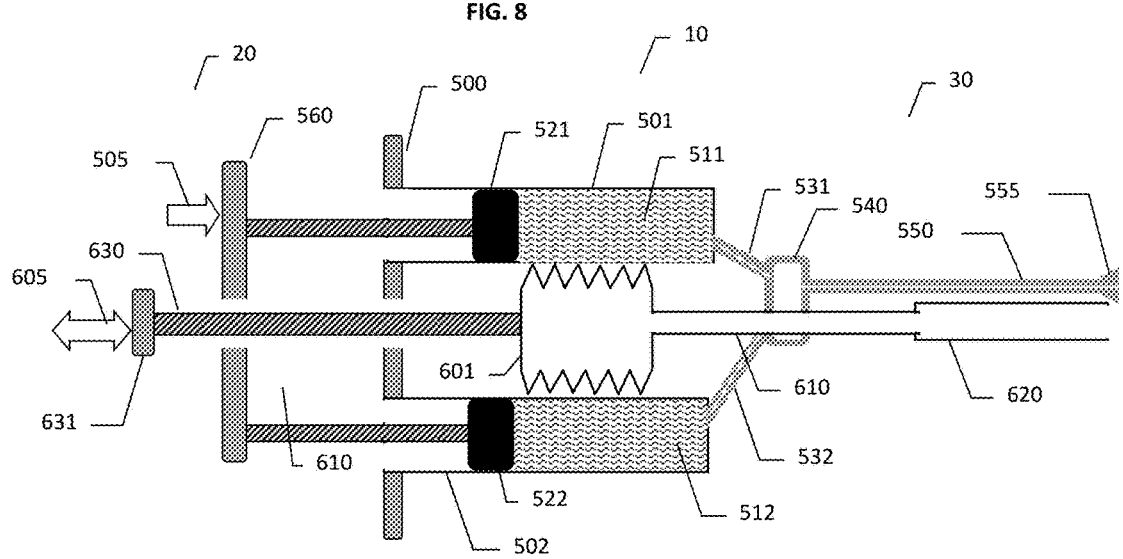

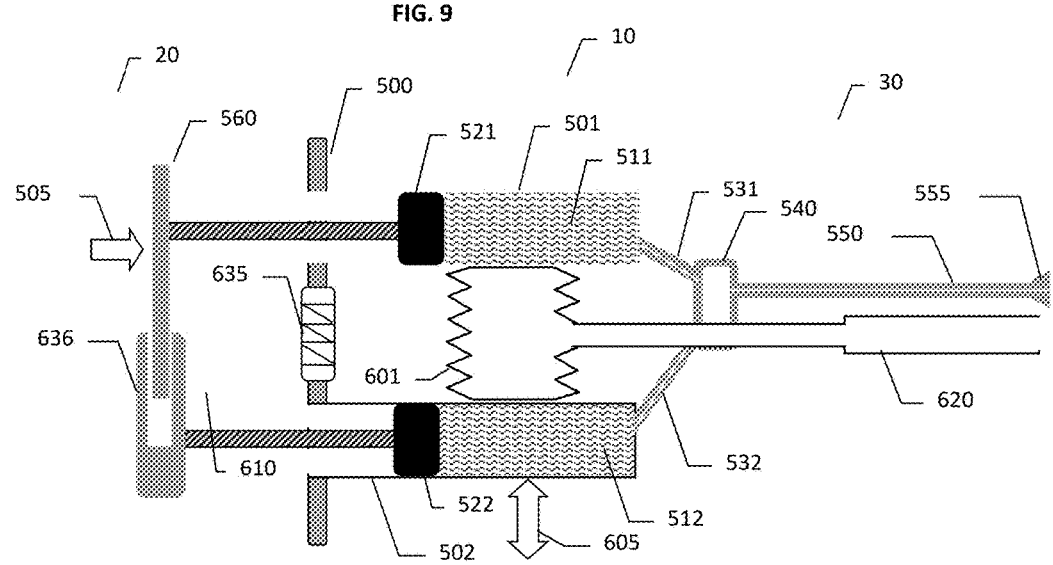
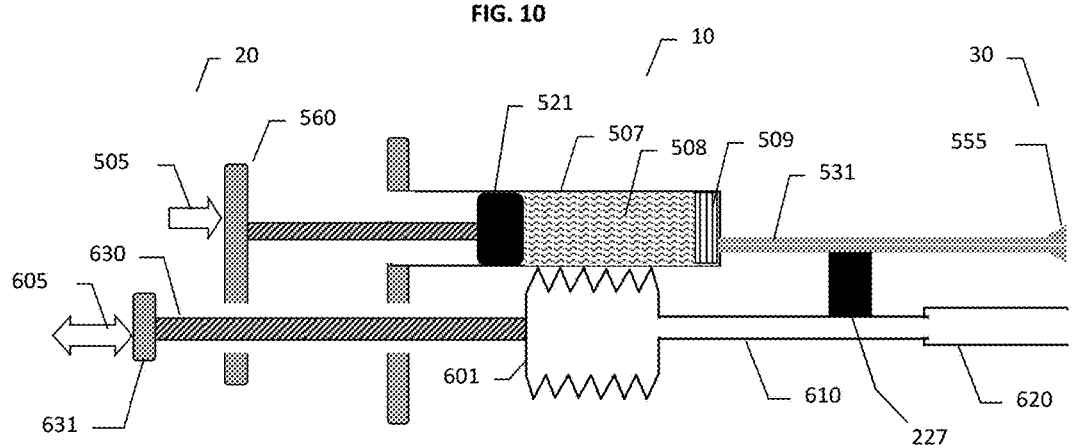

METHODS AND DEVICES FOR CO-DELIVERY OF LIQUID AND POWDERED HEMOSTATS AND SEALANTS

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin, collagen, chitin, chitosan, starch, etc. To improve the hemostatic performance, scaffolds based on the above materials can be combined with biologically-derived clotting factors, such as thrombin and fibrinogen.

The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. A number of methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber.

U.S. Pat. No. 7,923,031 "Haemostatic sprays and compositions" discloses a powder delivery system comprising: a chamber storing a haemostatic composition comprising dry gelatin powder having a mean particle size in the range of 30-250 micrometers and hyaluronic acid, said chamber having at least one discharge opening sized for distributing said composition.

U.S. Pat. No. 8,056,762 discloses a hand-held dispenser for dispensing a pharmaceutical product, the dispenser comprising: a housing providing a duct; a frangible membrane provided in the duct; a probe with a piercing tip mounted in the duct, the probe being arranged such that, in use, the piercing tip pierces the frangible membrane; an air compression device to compress air for expelling a pharmaceutical product through the probe; and a channel to substantially equalize the pressure in the air compression device and the pressure above the frangible membrane, wherein the frangible membrane is provided on a sheath which comprises a first larger diameter portion and a second axially spaced smaller diameter portion defining an external shoulder therebetween, and the inside surface of the duct has a corresponding internal shoulder to be engaged by the external shoulder of the sheath and an axial spacer is provided on one or both of the external and internal shoulders to maintain the channel past the engaged shoulders.

U.S. Patent publication No. 2012/108509 "Artificial Scab For Use In An Airway" discloses a bellows-type dispenser.

U.S. Patent publication No. 2011/0178495 "Internal dry powder delivery system and method thereof" discloses powder supply device that comprises a gas powder mixer providing a gas powder mixing chamber and a powder dispenser (bellow) which is screwed to the gas powder mixer and communicated with the gas powder mixing chamber therein. The hemostat powder is filled in the powder dispenser (bellow) and is adapted to be delivered via the powder delivery catheter to the site of bleeding.

U.S. Pat. No. 4,411,656 "Compressible syringe" discloses a compressible syringe comprised of a hollow body which is made compressible by bellow structures which extend the entire length of body.

U.S. Pat. No. 4,723,691 "Powder dispenser" discloses a hand-held and hand-operable powder dispenser having a container including a handle/nozzle section terminating at its discharge end in an unobstructed powder dispensing opening, a hand gripping section, and a central, flexible bellows section coupled between the handle/nozzle section and the hand-gripping section. The bellows section is adapted to be collapsed and expanded axially to serve as a pump. The inside diameters of the handle/nozzle section decrease substantially linearly and continually as a function of the length of the handle/nozzle section in a direction toward the powder dispensing opening. The ratio of the length of the handle/nozzle section to the greatest value of its inside diameter is substantially greater than 1.4.

U.S. Pat. No. 3,844,284 discloses a disposable douche comprised of a collapsible bellows forming a syringe and containing a pre-measured amount of cleansing powder and an elongated dispensing nozzle adapted to be secured to an open end of the bellows.

U.S. Pat. No. 5,957,340 "Container with surmounting bellows pump" discloses a container for storing and for positively dispelling and delivering therefrom fluid compositions contained therein, said container comprising a body defining a fluid reservoir, said body including a floor-like base, and walls extending upwardly thereof, a vertically-compressible bellows integrally formed with and surmounting said walls of said container as a coaxial extension thereof, said bellows defining an interior zone in fluid flow communication with said fluid reservoir of said container, a neck-like collar integrally formed with, and coaxial with, and mounted on said bellows at an upper limit thereof, said collar being formed with an upwardly-opening port through which said container is filled, cap-like closure means for sealing said port after introduction of a fluid composition into said reservoir, tubular conduit means including dispenser tube means integrally formed with and supported exteriorly of and radially outwardly of diametric bounds of said container for establishing fluid flow communication with said reservoir at a locale adjacent said base of said container, said conduit means projecting upwardly of said base and extending within vertical limits consistent with upper and lower bounds of said body of said container, said conduit means having a terminal discharge end, a nozzle integrally formed with said dispenser tube means at said terminal discharge end thereof, orifice means at said terminal discharge end of said conduit means for delivery of a fluid composition positively dispelled from said reservoir upon application of downwardly-directed, manually impressed compression forces to said bellows of said container, web means projecting outwardly of and extending along said wall means for connecting said wall means with said tubular conduit means for supporting and for stabilizing said conduit means; and said web means being integrally formed with said wall means and with said conduit means, and extending along an upward reach of said conduit means.

Patent Publication No. CN201346338 "Surgery styptic powder unidirectional propeller" discloses a surgery styptic powder unidirectional propeller, which belongs to a propeller structure attached to an endoscope, is used for delivering forwards styptic powder and comprises an inserted tube and a flexible drug-feeding bottle, wherein the inserted tube is butted and communicated with the flexible drug-feeding bottle; and the styptic powder is placed in the flexible drug-feeding bottle. The unidirectional propeller also comprises a unidirectional air inlet valve which is opened in the forward air inlet direction and is closed in the backward air inlet direction. The unidirectional propeller has the advantages that the unidirectional air inlet valve is combined with the inserted tube of a drug-feeding device for powder administration under the endoscope, thus effectively and quickly delivering the styptic powder to a required part, decreasing the reciprocation of the styptic powder in the inserted tube, preventing blood backflow and blockage and improving the styptic effect in the process of clinical endoscope surgery minimally invasive surgery; and biocompatible medical materials such as high density polyethylene, low density polyethylene, polypropylene, medical silicon rubber and the like are adopted to manufacture the propeller.

Reference is made to U.S. Patent publication No. 2014/0005636 "Multi-Compartment Pre-filled Mixing Syringes with Bypass" and to references cited therein; also a reference is made to commercially available Dermabond™ products and Evicel™ products.

U.S. Pat. No. 8,376,989 "Compartmented syringe" discloses a syringe, comprising: a first fluid conduit having at least two chambers for accommodating at least two substances of a plurality of substances and at least two bypasses operably coupled to the at least two chambers for enabling the at least two substances of the first fluid conduit to intermix; a second fluid conduit disposed adjacent the first fluid conduit and having at least one chamber for accommodating at least one substance of the plurality of substances; each substance being intermixable to form a discharge material for external application upon advancement of a plunger operably associated with each fluid conduit, the discharge material defined by the intermixed composition of predetermined volumes of at least two substances of the fluid conduits; and an end cap disposed on the distal end of at least one of the fluid conduits, the end cap including at least one vent and a filter, the filter in fluid communication with the at least one vent for facilitating the passage of gas from the end cap, the at least one vent defined through a wall of the end cap, the filter being disposed within the end cap and spaced from the at least one vent.

U.S. Pat. No. 7,946,417 "Curable material mixing and delivery device" discloses an apparatus and method for mixing two components and delivering the mixture to a patient. The apparatus contains a mixing chamber for mixing a liquid component and a powder component. The liquid component and powder component are mixed within the mixing chamber by rotation of a collapsible mixing element. A plunger is then advanced through the mixing chamber to force the mixture out of the mixing chamber and deliver the mixture to the patient.

U.S. Pat. No. 7,951,108 "Dual chamber mixing syringe and method for use" discloses a mixing syringe and method for using the mixing syringe are provided. The mixing syringe comprises a housing having a first compartment for containing a first component, an outer plunger having a second compartment for containing a second component, and an inner plunger. Prior to use, a seal separates the first and second components. To prepare the mixture, the seal is pierced and the two components are mixed. The mixing syringe and its method of use are particularly suited to applications in which at least one of the mixture components is a relatively highly viscous material.

U.S. Pat. No. 7,967,779 "Powder and liquid mixing syringe" discloses a mixing syringe having a first sealed chamber containing a powder (powder housing) and a second sealed chamber containing a liquid (liquid housing). When the user needs to inject a patient, the device is held approximately upright while depressing a plunger. This motion causes a piercing element to pierce a foil seal separating the two chambers. Liquid then drops down into the powder housing. The liquid flows through a passage in a piston located in the powder housing, where it then comes in contact with the powder itself. As the user continues pressing the plunger downward, the piercer comes to rest within the piston and seals the passage through the piston, thereby locking the piercer and piston together. The device is then ready for an injection. As the plunger is further depressed, the piston expels the powder and liquid mixture through a needle.

U.S. Pat. No. 6,458,095 "Dispenser for an adhesive tissue sealant having a housing with multiple cavities" discloses a dispenser for simultaneously dispensing first and second components of an adhesive tissue sealant, wherein at least the first component is stored in the dispenser as dry powder that is dissolved prior to use by introduction of a solvent, the dispenser comprising the combination of: (a) a first container comprising a first septum at one end, an open end opposite the first septum, and a first movable plug disposed therein, the first container containing a quantity of the first component in the form of a dry powder stored between the first septum and the first movable plug; (b) a second container comprising a second septum at one end, an open end opposite the second septum, and a second movable plug disposed therein, the second container containing a quantity of the second component; (c) a housing having a pair of cavities sized and configured to receive and support the first and second containers, each cavity having a base, (d) pistons sized and configured to be received in the open ends of the first and second containers to advance the first and second movable plugs; and the housing including a manifold sized and configured to fit over and pierce the first and second septums and to afford passage of the first and second components via first and second flow paths to a nozzle from which the first and second components are dispensed to combine to form the adhesive tissue sealant, first and second piercers mounted in the manifold for piercing the first and second septums, each piercer extending through and being supported by a disk that is supported adjacent the base of said each cavity, each disk being supported a distance spaced from the base of the first and second cavities to form first and second plenums, each plenum defined by said each disk and adjacent walls of said each cavity, the first and second piercers affording passage of the first and second components to the first and second plenums.

U.S. Pat. No. 6,699,229 "Fluid transfer device" discloses a fluid transfer and mixing device for use in the aseptic intermixing of a powder component with a fluid component. The device is of a simple, compact construction that includes a first adapter that can be easily connected to a container containing the powder component and a second adapter that can be removably interconnected with the first adapter and can also be readily connected to a container containing a fluid such as a diluent so as to permit aseptic intermixing of the diluent with the powder. In use a conventional needleless syringe can be easily connected to the first adapter so that the mixture of the powder and diluent can be aseptically aspirated from the first container for subsequent delivery to the patient.

Patent publication JP9182786A discloses an enema syringe to enable both liquid and powder enema to be injected that consists of an injection cylinder projected on one of the ends of a bellows-like cylinder, a puncturing means provided on the injection cylinder at the internal base end part of the bellows-like cylinder, and a powder storage bag and a liquid storage bag made of a pliable material respectively arranged sequentially from the base end part side of the injection cylinder in the bellows-like cylinder.

U.S. Pat. No. 369,767 discloses combined atomizer and syringe.

U.S. Patent publication No. 2011/0021982 "DISPENSING DEVICE WITH BYPASS" discloses a device for dispensing multiple components has a syringe housing comprising at least one storage container that is divided into at least two chambers and has a bypass arrangement, and a second storage container with or without a bypass arrangement, the syringe housing being realized as part of a double syringe or double cartridge having a double plunger and a common outlet. The bypass arrangement comprises at least two indentations.

U.S. Patent publication No. 2010/0219200 discloses an apparatus and method for mixing two components and delivering the mixture to a patient. The apparatus contains a mixing chamber for mixing a liquid component and a powder component. The liquid component and powder component are mixed within the mixing chamber by rotation of a collapsible mixing element. A plunger is then advanced through the mixing chamber to force the mixture out of the mixing chamber and deliver the mixture to the patient.

U.S. Patent publication No. 2003/0040701 "Dual chamber syringe with a dual function piston" discloses a dual chamber syringe in which a dual function piston divides the syringe into two compartments containing powder or fluid in one compartment and fluid in the other. For mixture of the two substances, a passage is opened between the two compartments before or during retraction of the piston to force the substances to be mixed in the front compartment. During forward movement of the piston, the passage between the two compartments is closed to force the mixture of substances through the discharge opening of the syringe.

SUMMARY OF THE INVENTION

The present invention is directed to an integrated delivery device that is operable with one hand and provides co-delivery of a liquid medicant and a powder medicant onto a tissue or wound from a liquid medicant expression subunit and a powder medicant expression subunit. Each expression subunit having an actuator for the liquid medicant and the powder medicant contained therein that are positioned in close proximity to one other at a proximate end of said expression subunits and delivery cannulas for each of said expression subunits that positioned in close proximity to one other at a distal end of said expression subunits. The integrated delivery device can have the liquid medicant expression subunit as a syringe and the powder medicant expression subunit as a powder delivery pump. The liquid medicant can be a two-part sealant or hemostat. The syringe can be a dual barrel syringe with each barrel containing one of different individual components of the two-part sealant or hemostat. The powder delivery pump can be a resiliently compressible bellows and a compartment filled with the powder medicant, said container being in fluid communication with the bellows and with the powder medicant delivery cannula. The dual barrel syringe can have two plungers that are connected by a plunger bridge at the proximal end and a handle at the proximal end, wherein the plunger bridge and the resiliently compressible bellows are positioned in close proximity to one another and are synchronously or sequentially operable while being held in one hand. The resiliently compressible bellows can be mounted onto the plunger bridge or onto the handle and further optionally mounted between the barrels. The plunger bridge and the resiliently compressible bellows are preferably operable with the same finger of one hand while being held in the same one hand.

In an alternative embodiment, the liquid medicant is a cross-linkable polymer in which the syringe comprises a single barrel syringe containing a cross-linking initiator and/or a cross-linking accelerator that is retained on a porous media that is in fluid communication with said single barrel syringe. The cross-linkable polymer can be an acrylic monomer.

The present invention also relates to method for using such integrated devices. In one embodiment, the liquid medicant and the powder medicant are delivered within about 10 seconds of each other onto the tissue, and wherein the integrated delivery device is operated with one hand. The resulting coating can have a tissue interface side and an opposing top side in which the powder medicant is directionally concentrated within the coating either at the tissue interface side or at the top side. In an alternative embodiment, the resulting coating has a tissue interface side and an opposing top side wherein the powder medicant is distributed approximately uniformly within the coating as between the tissue interface side and the top side.

In another embodiment, the powder medicant comprises a bioabsorbable powder having at least one of hemostatic, wound treatment, fluid absorption, properties, the liquid medicant comprises a rapidly curable bioabsorbable liquid having hemostatic and or tissue sealing properties and the powder medicant is a non-curable powder material. The powder medicant can be in the form of particles with an aspect ratio from about 1 to about 10 and an average particle size from about 90 microns to about 320 microns. The powder medicant can be selected from the group selected from oxidized cellulose, oxidized regenerated cellulose, chitosan, starch, gelatin, collagen, synthetic polymers and mixtures thereof. The powder medicant is preferably oxidized regenerated cellulose. In another embodiment, the liquid medicant comprises a fibrinogen and an initiator of fibrinogen conversion to fibrin. In a still further embodiment, the liquid medicant comprises an acrylic monomer.

BRIEF DESCRIPTION OF THE DRAWINGS

FIGS. 3a and 3b illustrate the steps of forming coatings of the present invention when the liquid medicant is delivered first followed by the powder medicant.

FIG. 4 illustrates the steps of forming coatings of the present invention when the liquid medicant is co-delivered synchronously with the powder medicant.

FIG. 5 illustrates the steps of forming coatings of the present invention when the powder medicant is delivered first followed by the liquid medicant and then followed by the powder medicant again.

FIG. 7 is a schematic cross-sectional view of an embodiment of the delivery device of the present invention.

FIG. 8 is a schematic cross-sectional view of an embodiment of the delivery device of the present invention.

FIG. 9 is a schematic cross-sectional view of an embodiment of the delivery device of the present invention.

FIG. 10 is a schematic cross-sectional view of an embodiment of the delivery device of the present invention.

DETAILED DESCRIPTION

Figure 1:
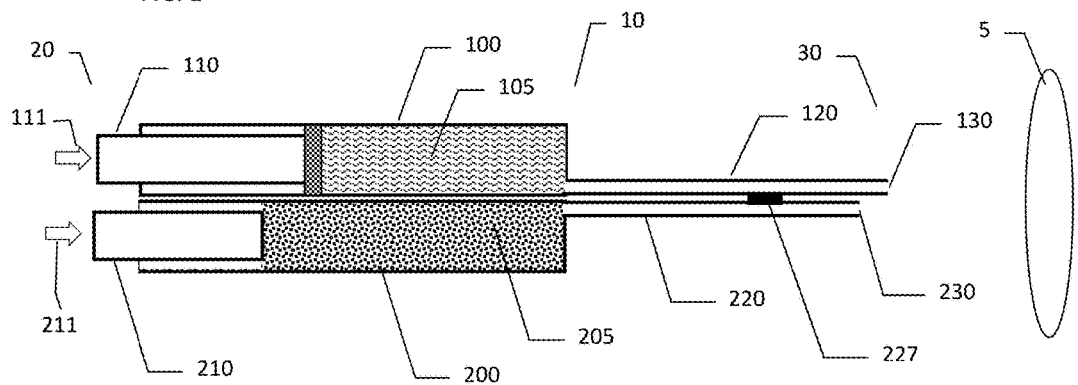
FIG. 1 is a schematic sketch of the delivery device of the present invention.
Figure 2A:
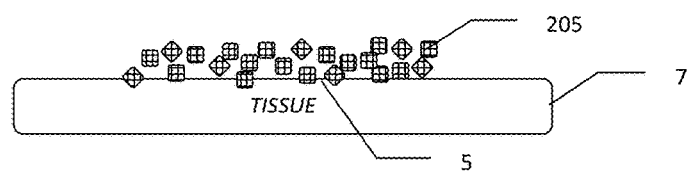
FIGS. 2a and 2b illustrate the steps of forming coatings of the present invention when the powder medicant is delivered first followed by the liquid medicant.
Figure 2B:
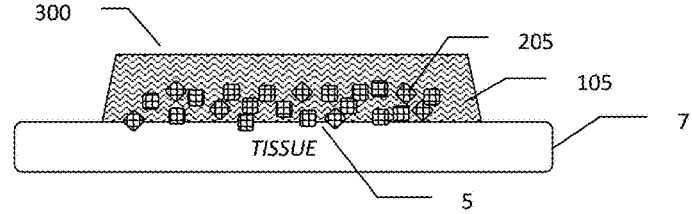

A number of liquid medicants and dry powder medicants for the delivery onto a tissue, particularly onto a wound during surgical procedures, are known and are widely used for beneficial wound treatment, including but not limited to sealing, hemostasis, healing, anti-microbial treatment, and combinations thereof. Such medicants, to name a few, include dry powders, such as oxidized regenerated cellulose (ORC), oxidized cellulose (OC), starch, chitosan and liquids, including biologics based liquids, such as thrombin, fibrinogen, thrombin/fibrinogen mixtures (forming fibrin glue), and synthetic based liquids, such as octylcyanoacrylates.

Pre-mixing of the powdered and liquid medicaments and then delivery of the resulting mixture onto the wound is known, but has certain disadvantages, including detrimental changes in desirable properties such as adhesivity and flowability, difficulties in spraying, premature setting of the material, and clogging of the delivery nozzles. Also, once dry powder is pre-mixed with the liquid medicament, the unique properties of the powder as dry and absorbent powder are significantly changed, which could render the desirable effects of the dry powder on the wound diminished.

Use of individual and separate devices to deliver dry powder and liquid medicants individually to the wound is possible. However such application presents the health practitioner with several difficulties. Operating and correctly targeting two independent delivery devices towards the same tissue area is difficult. Operating two separate delivery devices requires use of two hands for each device and additional dexterity related to triggering release from two separate systems and may require two health practitioners to administer. Further, inserting and targeting two separate delivery nozzles through one laparoscopic port is difficult. Sequentially delivering liquid and dry powder medicants by initially inserting a first device, delivering a first medicant (such as dry powder), then withdrawing the first device, inserting a second device, delivering the second medicant (such as liquid medicant), and removing the second device is time consuming, presents difficulties in targeting the same area, and most importantly may result in washing away or premature curing of the first medicant by the time the second medicant is delivered.

Time for inserting and removal in laparoscopic procedures of separate non-integrated devices can be comparable to time of curing of the two-part sealant or hemostat, such as a fibrin glue. It is estimated that removal of one device and insertion, visualization, positioning, and targeting of another device may take 2 minutes or more. Simultaneous delivery using separate non-integrated devices through either the same trocar or two different trocars presents difficulties for targeting the same spot on the tissue and also requires use of at least two hands, thus preventing the health practitioner from using other surgical tools. Use of two different trocars for laparoscopic delivery of a powder medicant and liquid medicant presents difficulties in exact targeting the same area and also requires an additional trocar insertion, which might be undesirable.

Since removal of one device and insertion, visualization, positioning, and targeting of another device may take 2 minutes or more, it may result in washing away of the powdered medicant if it was delivered first or in premature curing of the liquid medicant if it was delivered first, as most curable hemostats and sealants start curing immediately upon delivery and may form fully or partially cured coatings in well under two minutes. It is estimated that fibrin glue will partially cure, depending upon conditions and mixture type, in about 30 seconds, resulting in formation of a film preventing full integration and interaction with the powdered medicant.

Dry powder provides some unique properties for treating tissue in the wet field, particularly related to absorbent and hemostatic properties of dry powders, particularly ORC based powders. However dry powder has only very limited sealing and adhesion capacity on the tissue. On the other hand, liquid medicants, such as medicants forming fibrin, require time for polymerization or curing and can benefit from reinforcement provided by dry powder or fibrous materials. Thus it is highly desirable to provide a device which will enable single-hand operated delivery device for co-delivery of a powdered and a liquid medicant onto a tissue.

The present invention relates to a disposable dispensing apparatus for co-delivering a powdered and a liquid medicant onto a tissue, for wound treatment, sealing, hemostasis, anti-microbial treatment, and combinations thereof, with particular suitability to applications related to open surgical procedures; laparoscopic surgical procedures; or natural orifice translumenal endoscopic surgery procedures, providing for an easy to use and sterilized disposable device, operable by a health practitioner with one hand. In particular there is provided a single-use dry powder and liquid medicament co-delivery device which can be easily deployed laparoscopically through one laparoscopic port and operated for sequential or synchronous co-delivery of powdered and liquid medicaments without their prior mixing. A device for co-delivery comprises liquid medicant expression means integrated with powder medicant expression means.

The present invention further relates to a reinforced coating formed by co-delivering a powdered and a liquid medicant onto a tissue without pre-mixing said medicants prior to delivery resulting in on-tissue combination of powder or particulate material and liquid hemostat/sealant.

The present invention further relates to a method of forming a reinforced coating by co-delivering a powdered and a liquid medicant onto a tissue in a sequential or synchronous manner without pre-mixing.

Particles of dry powder can advantageously provide coating reinforcement properties; hemostatic properties; and liquid absorption properties, thus facilitating use of liquid sealants which are challenged in wet field.

Referring now to FIG. 1, delivery device 10 is presented in a schematic sketch and comprises, integrated together, a liquid medicant expression subunit 100 (such as a syringe) and a powder medicant expression subunit 200, subunits 100 and 200 are at least partially filled with liquid medicant 105 and powder medicant 205 respectively. At a proximate end 20, which is generally furthest away from targeted area on tissue 5, there are provided, in close proximity, expression actuators 110 for liquid medicant and 210 for powder medicant. At a distal end 30, which is generally closest to the targeted area 5 on tissue or wound, where the medicants are being delivered, are disposed, in close proximity to each other, delivery cannula 120 for liquid medicant 105 and delivery cannula 220 for powder medicant 205, with delivery cannulas having open ends or nozzles 130 and 230 at the distal end 30 through which open ends or nozzles 130 and 230 liquid medicant 105 and powder medicant 205 are respectively expressed. Delivery cannula 120 for liquid medicant 105 and delivery cannula 220 for powder medicant 205 can be integrated, i.e. formed as a single unit or have a joint 227 at one point of their lengths. Open ends or nozzles 130 and 230 can be positioned at the same distance from targeted area 5 or at a different distance (as shown in FIG. 1). According to one aspect of the invention, nozzle 130 of delivery cannula 120 for expression of liquid medicant 105 is positioned closer to targeted area 5 relative to nozzle 230 for expression of powder medicant 205, as shown in FIG. 1. This structure prevents liquid medicant 105 from getting onto or into nozzle 230 and consequently plugging nozzle 230.

It is to be understood that liquid medicant expression subunit 100 can comprise means for expressing one component liquid medicant, or a multiple component liquid medicant. In one aspect of the present invention, liquid medicant expression subunit 100 is a syringe-like device containing a cyanoacrylate based sealant or adhesive. In another aspect of the present invention, liquid medicant expression subunit 100 comprises a means for co-expressing a multiple component liquid medicant, wherein said means can be a dual barrel syringe with each barrel containing one component of a two-part sealant, adhesive, or hemostat, such as when a first barrel contains a polymerizable material, and a second barrel contains a polymerization initiator, activator, or catalyst. In one aspect, one barrel contains fibrinogen, and another barrel contains thrombin or another fibrinogen activator, with fibrinogen and thrombin mixed immediately prior to the expression from nozzle 130 or are sprayed unmixed. The expression ratio or a mixing ratio of fibrinogen and thrombin is defined by the diameters of the barrels, and can vary from 1:1 to 5:1 to 1:5.

In use, a health practitioner can optionally use two hands to operate device 10, with one hand holding the device and another hand actuating expression actuators 110 for liquid medicant and 210 for powder medicant thus expressing liquid medicant 105 and powder medicant 205 from open ends 130 and 230 towards targeted area 5. Preferably, health practitioner uses one hand to operate device 10, grasping the device and using for instance, a thumb of the same hand for actuating expression actuators 110 for liquid medicant and 210 either synchronously or sequentially. Actuation of expression actuators 110 for liquid medicant and 210 for powder medicant is schematically shown by arrows 111 and 211 respectively. Mixing and interaction of liquid medicant 105 and powder medicant 205 is occurring on tissue or optionally during deposition as these medicants travel from nozzles 130 and 230. No mixing of liquid medicant 105 and powder medicant 205 occurs prior to expression of these medicants. Mixing prior to expression of the medicants could result in clogging and reduced operability of device 10.

Referring now to FIGS. 2-5, the steps of forming various coatings of the present invention are shown and illustrated. FIG. 2 shows formation of a coating when powder medicant 205 is delivered first. FIG. 2*a* shows powder or particulate medicant 205 being delivered first; it then optionally absorbs liquid and/or provides hemostatic effect on wound or tissue 7 targeted area 5. FIG. 2*b* shows liquid medicant 105, such as sealant, immediately delivered on top of powder medicant 105, thus forming a coating 300 having powder-enriched layer on the tissue 7 surface, said coating acting as reinforced hemostat/sealant. Health practitioner is actuating expression actuator 210 for powder medicant thus expressing the powder medicant 205 and then immediately actuating expression actuator 110 for liquid medicant 105 thus forming coating 300. No mixing of liquid medicant 105 and powder medicant 205 occurs prior to expression of these medicants.

FIG. 3 shows formation of a coating when the liquid medicant is delivered first. FIG. 3*a* shows liquid medicant 105 being delivered first, establishing a bond at the tissue 7 targeted area 5 interface, and starting forming a polymerized coating over wound or targeted area 5. FIG. 3*b* shows powder medicant 205 immediately delivered on top of liquid medicant 105 while it is curing/crosslinking, and prior to full cure/cross-linking, with at least some powder medicant 205 embedding into liquid medicant 105, thus forming a coating 305 having a powder-enriched layer on the coating surface not interfacing with tissue 7, said coating 305 acting as reinforced hemostat/sealant. In this embodiment of coating formation, powdered or particulate medicant 205 provides reinforcement of the top layer (i.e. not interfacing with tissue) of coating 305 without affecting tissue bonding. Health practitioner actuates expression actuator 110 for liquid medicant 105 and then immediately actuates expression actuator 210 for powder medicant thus expressing powder medicant 205, thus forming coating 305. No mixing of liquid medicant 105 and powder medicant 205 occurs prior to expression of these medicants.

FIG. 4 shows formation of a coating when powder medicant 205 and liquid medicant 105 are delivered substantially simultaneously. Health practitioner actuates expression actuator 210 for powder medicant 205 simultaneously with expression actuator 110 for liquid medicant 105, thus co-expressing or co-spraying powder medicant 205 and liquid medicant 105, which then intermix and intermingle during and upon deposition onto tissue 7 thus forming coating 307 having powder distributed throughout the coating. In another aspect, health practitioner actuates expression actuator 210 for powder medicant 205 in short busrts intermittently with actuating expression actuator 110 for liquid medicant 105 in short bursts, thus co-expressing or co-spraying powder medicant 205 and liquid medicant 105, which then intermix and intermingle during and upon deposition onto tissue 7. No mixing of liquid medicant 105 and powder medicant 205 occurs prior to expression of these medicants.

FIG. 5 shows formation of a coating when powder medicant 205 and liquid medicant 105 are delivered one after another in several bursts, resulting in "layered" delivery. Health practitioner intermittently actuates expression actuator 210 for powder medicant 205, followed by actuating expression actuator 110 for liquid medicant 105, again followed by actuating expression actuator 210 and then followed by actuating expression actuator 110, and repeating these steps as needed. As a result, a layered coating 309 forms that has several layers of coating 309 enriched with powder medicant 205, as shown in FIG. 5. In another aspect of the invention (not shown), health practitioner actuates expression actuator 110 for liquid medicant 105, followed by actuating expression actuator 210 for powder medicant 205, again followed by actuating expression actuator 110 and then followed by actuating expression actuator 210, and repeating these steps as needed. As a result, a layered coating forms that has several layers of coating enriched with powder medicant 205.

Figure 6A:
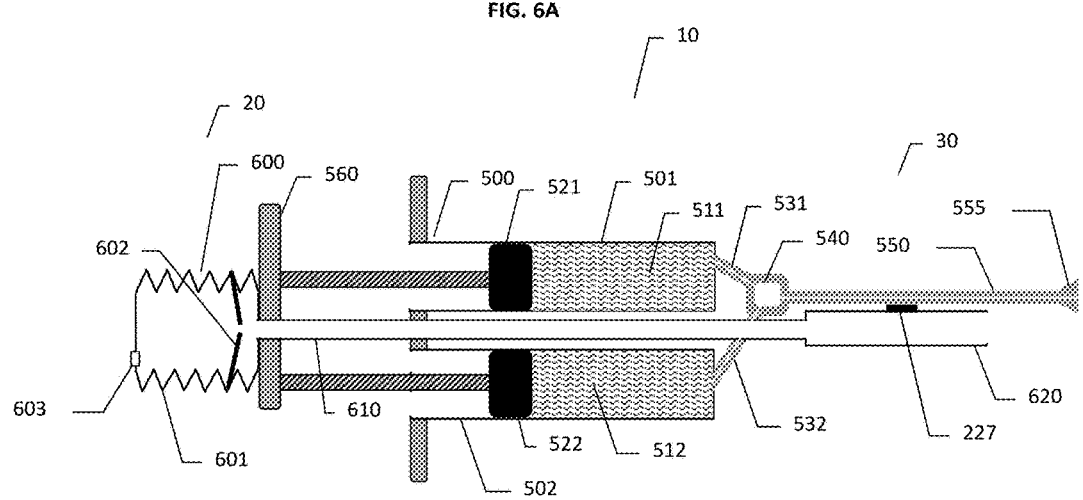
FIGS. 6A-6D is a schematic cross-sectional view of different aspects of the delivery device of the present invention.

Referring now to FIG. 6A, in one aspect of the present invention, delivery device 10 is shown in a schematic cross-sectional view comprising liquid medicant expression subunit comprising a dual barrel syringe 500 integrated with powder medicant expression subunit comprising a bellows based powder delivery pump 600. Dual barrel syringe 500 comprises first barrel 501 containing first liquid component 511 and second barrel 502 containing second liquid component 512 of two-part polymerizable sealant. Plungers 521 and 522 are provided for expressing first liquid component 511 and second liquid component 512 from dual barrel syringe 500 via exit ports or conduits 531 and 532 towards optional mixer 540 where first liquid component 511 and second liquid component 512 intermix initiating polymerization or cross-linking reaction then continuing expression via delivery cannula 550, with the mixed first liquid component 511 and second liquid component 512 exiting delivery device 10 at the distal end 30 via spray nozzle 555 situated at the distal end 30 of delivery cannula 550. Plungers 521 and 522 are simultaneously actuated by a unified actuator or plunger bridge 560 positioned at the proximal end 20.

A number of different powder delivery pumps can be utilized in delivery device 10. According to one aspect of the present invention, powder delivery pump 600 comprises bellows 601 with an optional powder one way valve 602 disposed within bellows 601. Powder one way valve 602 in one aspect comprises a flexible membrane having a slit. An optional air intake one way valve 603 is located on distal end 20 of bellows 601. Optional air intake one way valve 603 can be also located anywhere on bellows 601 or on powder expression cannula 610. Optional air intake one way valve 603 in one aspect comprises a flexible membrane having a slit. Powder expression cannula 610 connects bellows 601 to powder expression nozzle 620 at the distal end 30. Delivery cannula 550 or spray nozzle 555 can be optionally connected or integrated with powder expression nozzle 620 or powder expression cannula 610. As shown in FIG. 6A, joint 227 is optionally connecting delivery cannula 550 with powder expression nozzle 620 for better structural integrity.

In one aspect of the present invention, powder expression cannula 610 is flexible to allow for advancement of bellows 601 together with plunger bridge 560 on which it is mounted, towards distal end upon expression of first liquid component 511 and second liquid component 512. In another aspect of the present invention, powder expression cannula 610 is not flexible and bellows 601 does not advance together with plunger bridge 560 towards distal end.

Preferably, powder delivery pump 600 is integrated with dual barrel syringe 500, whereby bellows 601 is located in close proximity to plunger bridge 560 or mounted onto plunger bridge 560 as shown. Such structure enables convenient actuation of delivery device 10 by health practitioner for co-delivery of liquid medicant and powder medicant in any sequential or synchronous scenarios described above.

Figure 6B:
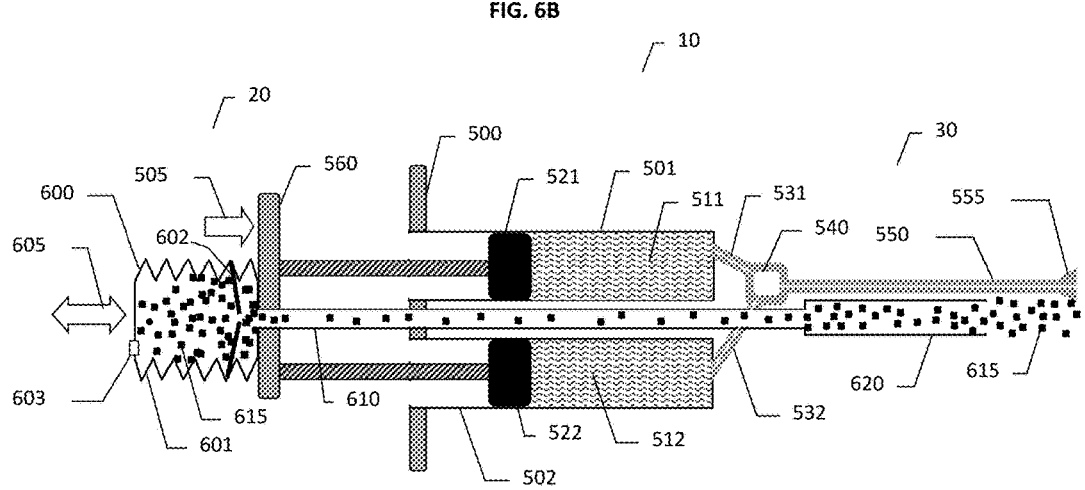

Referring now to FIG. 6B, delivery device 10 is shown with powder particles 615 contained in bellows 601 as well being expressed through powder expression cannula 610 and via powder expression nozzle 620. Actuation of powder delivery pump 600 is schematically shown by two-sided arrow 605 indicating back and forth actuating pressure exerted by the user, resulting in air and powder within bellows 601 moving through powder expression cannula 610 and exiting via powder expression nozzle 620. Actuation of plungers 521 and 522 by exerting pressure on plunger bridge 560 is schematically shown by arrow 505, results in simultaneous expression of first liquid component 511 and second liquid component 512 from delivery device 10 via nozzle 555.

In one aspect of the present invention, health practitioner holds delivery device 10 in one hand and uses the thumb of the same hand to actuate powder delivery pump 600 as shown by arrow 605. Prior to such actuation, after such actuation, or synchronously with such actuation, health practitioner also actuates plungers 521 and 522 by exerting pressure on plunger bridge 560 as schematically shown by arrow 505, using the same thumb. In one aspect of the present invention, health practitioner actuates powder delivery pump 600 by depressing bellows 601 using the thumb, and then continues depressing bellows 601 to exert additional pressure through compressed bellows 601 onto plunger bridge 560 thus expressing first liquid component 511 and second liquid component 512 from delivery device 10 after expressing powder particles 615.

It is to be understood that optional powder one way valve 602 enables powder 615 to exit bellows 601 when bellows 601 are pressurized and prevents powder 615 from exiting when bellows 601 is not pressurized. In another embodiment (not shown), optional powder one way valve 602 is positioned within cannula 610.

It is to be understood that optional air intake one way valve 603 causes bellows 601 to refill with air once pressure on bellows 601 is released; presence of air intake one way valve 603 enables air in the vicinity of proximal end 20 to refill bellows 601 instead of air in the vicinity of distal end 30, which air would enter bellows 601 via powder expression nozzle 620 and powder expression cannula 610. In the absence of optional air intake one way valve 603, clogging of powder expression nozzle 620 and powder expression cannula 610 is more probable. In another embodiment (not shown), optional air intake one way valve 603 is positioned on powder expression cannula 610.

In one aspect of the present invention, first liquid component 511 is fibrinogen solution, and second liquid component 512 is thrombin or another fibrinogen activator solution, with fibrinogen and thrombin mixing resulting in formation of fibrin.

Figure 6C:
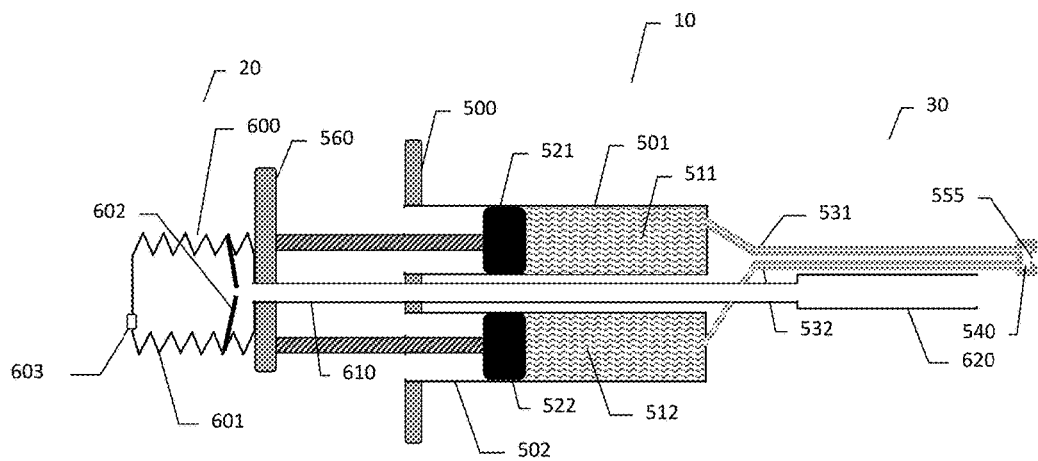

In one aspect of the present invention, and referring to FIG. 6C, mixer 540 is positioned at the distal end 30 and terminates in spray nozzle 555. Optionally, as shown in FIG. 6C, mixer 540 and spray nozzle 555 are structurally unified and represent a spray nozzle having a mixing chamber as known in the art.

Figure 6D:
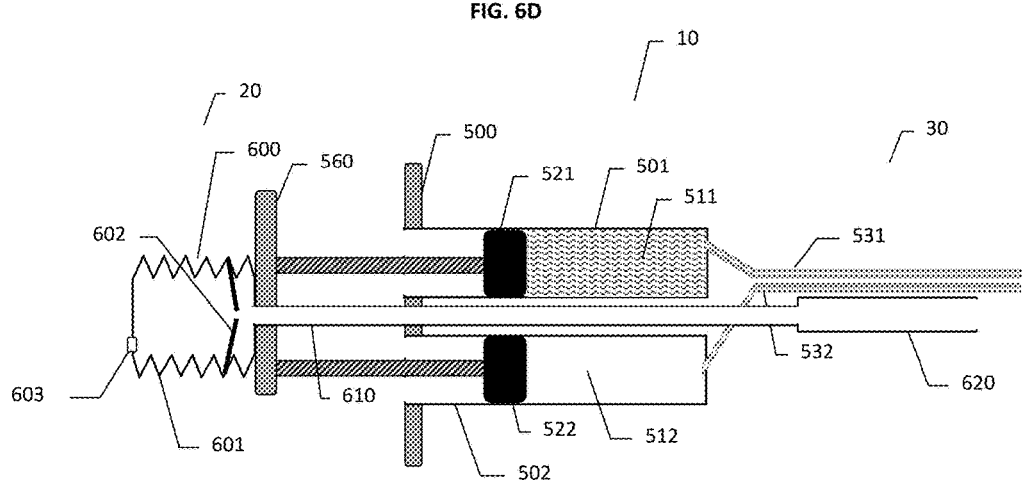

In one aspect of the present invention, and referring to FIG. 6D, delivery device 10 has no mixer 540 and no spray nozzle 555, with first liquid component 511 and second liquid component 512 expressed directly via exit ports or conduits 531 and 532 without mixing.

In another aspect of the present invention, and referring to FIG. 7, powder delivery pump 600 is integrated with dual barrel syringe 500 with bellows 601 located in close proximity to plunger bridge 560 but fixedly mounted onto dual barrel syringe 500 handle 503. Powder expression cannula 610 can be either rigid or flexible. In this aspect of the invention, powder delivery pump 600 and bellows 601 are not advancing together with plunger bridge 560 towards distal end 30.

In this aspect of the present invention, health practitioner holds delivery device 10 in one hand and is using the thumb of the same hand to actuate powder delivery pump 600 as shown by arrow 605. Prior to such actuation, after such actuation, or synchronously with such actuation, health practitioner also actuates plungers 521 and 522 by exerting pressure on plunger bridge 560 as schematically shown by arrow 505, using the same thumb.

In further aspect of the present invention, there is provided a conduit (not shown) for supplying compressed air to facilitate mixing and spraying of first liquid component 511 and second liquid component 512, with air conduit connected to spray nozzle 555 or terminating in an air outlet in the vicinity of spray nozzle 555 or in the vicinity of exit ports or conduits 531 and 532, as known in the art.

In another aspect of the present invention, there is provided a conduit (not shown) for supplying compressed air to powder delivery pump 600 with conduit connected to bellows 601 or to powder expression cannula 610 to facilitate expression of powder 615. In yet another aspect of the present invention, conduit (not shown) for supplying compressed air is terminating in an air outlet in the vicinity of powder expression nozzle 620 at the distal end 30 to facilitate powder 615 expression.

In a further aspect of the present invention, and referring to FIG. 8, bellows 601 are situated between barrels 501 and 502 (as shown) or on the side of barrels 501 and 502 (not shown), with bellows 601 actuating bar 630 extending through plunger bridge 560 and terminating in handle 631. Actuation of bellows 601 is schematically shown by two-sided arrow 605 indicating back and forth actuating pressure exerted by the user, resulting in air and powder within bellows 601 moving through powder expression cannula 610 and exiting via powder expression nozzle 620. Actuation of plungers 521 and 522 by exerting pressure on plunger bridge 560 is schematically shown by arrow 505, resulting in simultaneous expression of first liquid component 511 and second liquid component 512 from delivery device 10 via nozzle 555.

As illustrated above, in one aspect of the present invention, health practitioner holds delivery device 10 in one hand and is using the thumb of the same hand to actuate bellows 601 as shown by arrow 605 via actuating bar 630 through exerting and releasing pressure on handle 631. Prior to such actuation, after such actuation, or synchronously with such actuation, health practitioner also actuates plungers 521 and 522 by exerting pressure on plunger bridge 560 as schematically shown by arrow 505, using the same thumb.

In one aspect of the present invention, and referring to FIG. 9, bellows 601 are situated between barrels 501 and 502 whereby barrels can be moved closer to each other or further from each other thus compressing and decompressing bellows 601. Barrels 501 and 502 are joined by flexible linkages 635 and 636 enabling moving barrels 501 and 502 closer together by squeezing them in one hand. Conduits 531 and 532 are flexible and not interfering with compressing and decompressing bellows 601 between barrels 501 and 502.

In use, health practitioner holds delivery device 10 in one hand and is using the thumb of the same hand to actuate plungers 521 and 522 by exerting pressure on plunger bridge 560 as schematically shown by arrow 505 thus expressing first liquid component 511 and second liquid component 512 from delivery device 10. Prior to such actuation, after such actuation, or synchronously with such actuation, health practitioner also, using the same hand holding dual barrel syringe 500, exerts and releases pressure on barrels 501 and 502 bringing them together and further apart, thus compressing and decompressing bellows 601, thus expressing powder medicant from delivery device 10.

In one aspect of the present invention, and referring to FIG. 10, delivery device 10 comprises a container 507, which can be of a syringe type, containing polymerizable sealant 508, such as cyanoacrylate based sealant, with a porous plug 509 impregnated with polymerization initiator or accelerator at the distal end 30 of container 507. Bellows 601 are integrated with container 507, with bellows actuating bar 630 extending through plunger bridge 560 and terminating in handle 631. Actuation of bellows 601 is schematically shown by two-sided arrow 605 indicating back and forth actuating pressure exerted by the user, resulting in air and powder within bellows 601 moving through powder expression cannula 610 and exiting via powder expression nozzle 620. Actuation of plunger 521 by exerting pressure on plunger bridge 560 is schematically shown by arrow 505, resulting in expression of polymerizable sealant 508 through porous plug 509 and then through conduit 531 via nozzle 555. Powder expression cannula 610 is optionally connected or integrated with conduit 531 via joint 227 for better structural integrity.

As illustrated above, in one aspect of the present invention, health practitioner holds delivery device 10 in one hand and is using the thumb of the same hand to actuate bellows 601 as shown by arrow 605. Prior to such actuation, after such actuation, or synchronously with such actuation, health practitioner also actuates plunger 521 by exerting pressure on plunger bridge 560 as schematically shown by arrow 505, using the same thumb.

Figure 11:
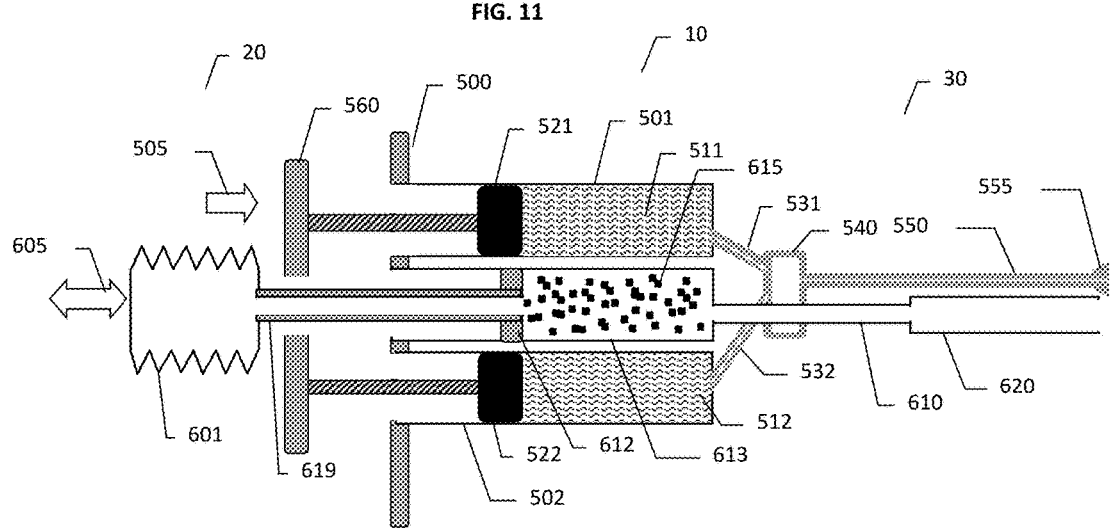
FIG. 11 is a schematic cross-sectional view of an embodiment of the delivery device of the present invention.

In one aspect of the present invention, and referring to FIG. 11, delivery device 10 comprises a dual barrel syringe 500 integrated with powder delivery pump comprising bellows 601 and powder containing syringe 613 positioned alongside barrels 501 and 502. Bellows 601 is mounted on rigid air cannula 619 which terminates in powder plunger 612 slidably positioned within powder containing syringe 613. Preferably, bellows 601 is located in close proximity to plunger bridge 560 as shown. Advantageously, such structure enables convenient actuation of delivery device 10 by health practitioner for co-delivery of liquid medicant and powder medicant in any sequential or synchronous scenarios described above.

Actuation of bellows 601 is schematically shown by two-sided arrow 605 indicating back and forth actuating pressure exerted by the user. This results in air moving from bellows 601 into air cannula 619 and then into powder containing syringe 613, with powder 615 then moving through powder expression cannula 610 and exiting via powder expression nozzle 620. Upon exerting further pressure on bellows 601 powder plunger 612 can advance within powder containing syringe 613 resulting in all available volume occupied by powder 615 within powder containing syringe 613, with expected advantageous improvement in the uniformity of the powder 615 expression. In one aspect, bellows 601 and plunger bridge 560 are not connected and can advance independently towards distal end 30 as expression of powder 615 and liquids 511 and 512 progresses. In another aspect, bellows 601 is fixedly mounted onto plunger bridge 560, resulting in bellows 601 and powder plunger 612 advancing the same distance as plungers 521 and 522 which are driven by plunger bridge 560. This arrangement advantageously results in improved control of volumetric co-expression of powder 615 and liquids 511 and 512.

Figure 12A:
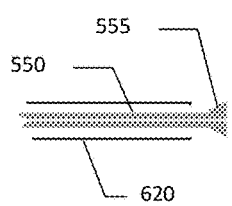
FIGS. 12A and 12B are views of mounting delivery cannula and spray nozzle in relationship to the powder expression nozzle of the present invention.
Figure 12B:
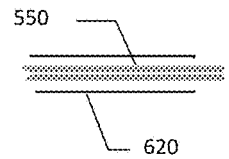

In one aspect of the present invention, as shown above, delivery cannula 550 and or spray nozzle 555 and or conduits 531 and 532 are mounted side by side with powder expression nozzle 620. In another aspect of the present invention, and referring to FIG. 12A, delivery cannula 550 and spray nozzle 555 are mounted co-axially with powder expression nozzle 620. Referring to FIG. 12B, delivery cannula 550 with no spray nozzle 555 is mounted co-axially with powder expression nozzle 620. Conduits 531 and 532 (not shown) can also be mounted co-axially with powder expression nozzle 620.

In one aspect of the present invention, device 10 is operable with one hand; in another aspect, device 10 is operable using two hands.

In one aspect of the present invention, dry powder medicants include any bioabsorbable powder or particulate material, such as polysaccharides, for instance, oxidized cellulose, oxidized regenerated cellulose, starch, and the like, gelatin, collagen, chitosan, synthetic materials such as based on lactide/glycolide and/or polydioxanone polymers or copolymers, and the like, minerals, etc.

In one aspect of the present invention, dry powder medicants are in the form of particles or fibers. In one aspect of the present invention, liquid medicant is one-part or two-part rapidly curable composition, such as fibrinogen/thrombin; acrylate-based, PEG-based, or protein-based. In one aspect, acrylate based composition is used, with curing initiator or accelerator added to the powdered medicant.

In one aspect, device 10 is utilized for laparoscopic delivery through a trocar.

In one aspect, air actuation is caused with pressurized gas ($CO_2$, air, $N_2$) or single use compressed gas container to force deliver powder medicant and/or fluid medicant or to facilitate spray of powder medicant and/or fluid medicant.

While the following examples demonstrate certain embodiments of the invention, they are not to be interpreted as limiting the scope of the invention, but rather as contributing to a complete description of the invention.

EXAMPLE 1

Peel testing was performed to compare various scenarios of co-depositing powder based and fluid based materials for tissue sealing and hemostasis.

A substrate of porcine liver was utilized for the in vitro test. Porcine plasma (Lampire Biological Laboratories, Porcine Plasma in Na Citrate) was sprayed (1 mL) onto an cross incision (5 cm long, and 2 cm cross cut at an 1 cm interval width) in the liver tissue, followed by placing a testing coupon consisting of flat oval-shaped wire ring, the wire having thickness of 0.8 mm; with width of oval 0.5 cm and length of oval 3 cm, with the test coupon placed flat onto tissue and connected to a hook orthogonally extending from the coupon perpendicular to tissue surface. As a powder component, ORC powder was used [Lot # RC032614-A, particle size distribution analyzed by QUIPIC particle imaging system is 94 um (d10), 183 um (d50), 320 um (d90) and the Hausner Ratio (based on USP 616) is 1.32]. Powder was made by a milling and roller compaction process similar to described in U.S. Published Patent Application 2013/0316974, incorporated by reference herein in its entirety. As a fluid components thrombin (commercially available from Ethicon, Inc. as EVITHROM™) and fibrinogen (or BAC2; commercially available from Ethicon, Inc. in EVICEL™ kits) were used with ratio of Thrombin to BAC2 (1:1, vol/vol).

Test samples were as follows:
T1: ORC powder with no fluid
T2: Fluid (Evicel) with no ORC powder
T3: Fluid (Evicel) followed by ORC powder within 120 sec
T4: ORC powder followed by fluid (EVICEL) within 10 sec
T5: Fluid (Evicel) followed by ORC powder within 5 sec
T6: Co-spray of ORC powder and fluid (Evicel) which then intermix on the surface of tissue The peel strength was then measured by a portable hanging scale (WeiHeng Portable Hanging Scale X000HY41J1; OHAUS Gold Series, YA501) within 2 minutes after the testing conditions were achieved by attaching the hanging scale to the hook and measuring the force required to peel the formed coating.

Figure 13:
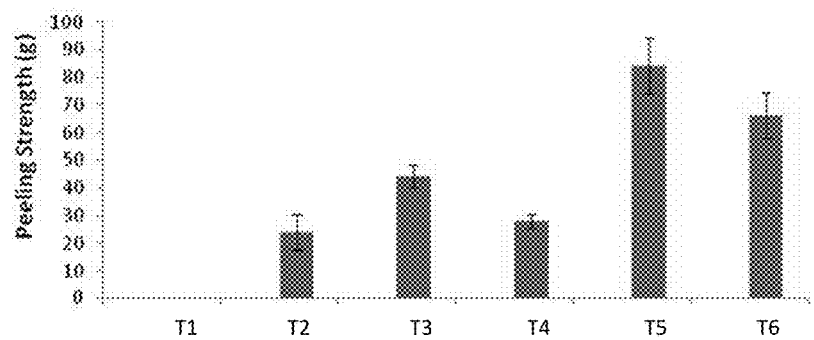
FIG. 13 shows the results of the peel test of the coatings of the present invention.

Peel test parameters and results are presented in Table 1 and in FIG. 13. Table 1 presents results of six testing conditions (T1-T6) and corresponding experimental setup parameters, including the amount of ORC powder used; amount of Evicel mixture used; as well as peel strength measured for 3 tests under each of six testing conditions, as well as average peel strength for each of six testing conditions. FIG. 13 presents average peel strength for each of six testing conditions.

TABLE 1

| Peel test parameters and results | | | | | | |
|---|---|---|---|---|---|---|
| | T1 | T2 | T3 | T4 | T5 | T6 |
| Plasma | 1 mL | 1 mL | 1 mL | 1 mL | 1 mL | 1 mL |
| ORC Powder (grams) | 0.3 g | N/A | 0.3 g | 0.3 g | 0.3 g | 0.3 g |
| EVICEL | N/A | 2 mL | 2 mL | 2 mL | 2 mL | 2 mL |
| Peel Strength (grams) | 0 | 30 | 40 | 25 | 95 | 75 |
| | 0 | 25 | 45 | 30 | 83 | 65 |
| | 0 | 17 | 48 | 29 | 75 | 59 |
| Average Peel Strength (grams) | 0 | 24 | 44 | 28 | 84 | 66 |

The results of testing presented in Table 1 demonstrate that powder (T1) and fluid (T2) on their own performed poorly in the peel test. Also powder followed by fluid (T4) was not showing significant improvements in the testing model. Fluid followed by ORC powder (T3) showed improved peel performance. Even more substantially improved performance was demonstrated by T5—Fluid followed by ORC powder within 5 sec and T6—co-spray of ORC powder and fluid.

As discussed above, time for inserting and removal in laparoscopic procedures of separate non-integrated devices can be comparable to time of curing of the two-part sealant or hemostat, such as a fibrin glue. It is estimated that removal of one device and insertion, visualization, positioning, and targeting of another device may take 2 minutes or more. Simultaneous delivery using separate non-integrated devices through either the same trocar or two different trocars presents difficulties for targeting the same spot on the tissue and also requires use of at least two hands, thus preventing the health practitioner from using other tools. The use of two different trocars for laparoscopic delivery of a powder medicant and liquid medicant presents difficulties in exact targeting the same area and also requires an additional trocar insertion, which might be undesirable. Since removal of one device and insertion, visualization, positioning, and targeting of another device may take 2 minutes or more, it may result in washing away of the powdered medicant if it was delivered first or in premature curing of the liquid medicant if it was delivered first. As shown in the Example 1, the strongest coatings with the highest peel strength were obtained with fluid medicant followed by powder within short period of time such as 5 sec or with the co-spray of powder and fluid medicant which then intermix on the surface of tissue.

EXAMPLE 2

Testing was performed on a substrate of porcine liver with no plasma present. Different compositions shown in Table 2 were deposited on the substrate with no plasma present. The resulting coatings were then manually peeled using duck head tweezers and ease of peeling manually estimated on a 0 . . . 5 scale. Compositions included
ORC powder with no fluid
Fluid (Evicel) with no ORC powder
Fluid (Evicel) followed by ORC powder within 120 sec
ORC powder followed by fluid (Evicel) within 10 sec
Fluid (Evicel) followed by ORC powder within 5 sec
Co-spray of ORC powder and fluid (Evicel) which then intermix on the surface of tissue
Co-spray of ORC powder and fluid (Evicel) followed by ORC powder

TABLE 2

Ease of peeling estimates with no plasma present, test parameters and results

|  | ORC powder | Evicel | Evicel spray followed by spraying ORC powder in approximate 120 seconds | ORC powder spray followed by Evicel | Evicel spray followed spraying by ORC powder in approximate 10 seconds | Co-spray ORC powder and Evicel | Co-spray ORC powder and Evicel follow by ORC powder spray |
|---|---|---|---|---|---|---|---|
| ORC Powder (grams) | 0.3 g | N/A | 0.3 g | 0.3 g | 0.3 g | 0.3 g | 0.3 g + 0.3 g |
| Evicel | N/A | 2 mL | 2 mL | 2 mL | 2 mL | 2 mL | 2 mL |
| Ease of peeling manual estimate (0 . . . 5 scale) | 0 | 0.5 | 1 | 1.5 | 1.5 | 4 | 4 |

The results of testing presented in Table 2 demonstrate that ORC powder followed by fluid (Evicel) and Fluid (Evicel) followed by ORC powder demonstrated enhanced peel strength. Further, co-spray of ORC powder and fluid (Evicel) as well as co-spray of ORC powder and fluid (Evicel) followed by ORC powder demonstrated even higher peeling strength as compared to ORC powder with no fluid and Fluid (Evicel) with no ORC powder.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

We claim:
1. An integrated delivery device operable with one hand and for co-delivery of a liquid medicant and a powder medicant onto a tissue or wound without pre-mixing said medicants prior to delivery, comprising at least two integrated medicant expression subunits of
   a) a liquid medicant expression subunit and a
   b) a powder medicant expression subunit,
      a. each expression subunit having an actuator for the medicant contained therein, the actuators are positioned in close proximity to each other at a proximate end of said expression subunits, and
      b. delivery cannulas for each of said expression subunits that positioned in close proximity to each other at a distal end of said expression subunits,
the delivery device configured so that no mixing of the liquid medicant and the powder medicant occurs prior to expression of both said medicants;
wherein the liquid medicant expression subunit comprises a syringe containing the liquid medicant, and the powder medicant expression subunit comprises a powder delivery pump;
wherein the liquid medicant comprises a two-part sealant or hemostat, and the syringe comprises a dual barrel syringe with each barrel containing one of different individual components of the two-part sealant or hemostat;
wherein the powder delivery pump comprises a resiliently compressible bellows and a compartment filled with the powder medicant, said compartment being in fluid communication with the bellows and with the powder medicant delivery cannula; and
wherein the dual barrel syringe comprises two plungers that are connected by a plunger bridge at the proximal end and a handle at the proximal end, wherein the plunger bridge and the resiliently compressible bellows are positioned in close proximity to one another and are synchronously or sequentially operable while being held in one hand.

2. The integrated delivery device of claim 1, wherein the resiliently compressible bellows is mounted onto the plunger bridge or onto the handle.

3. The integrated delivery device of claim 1, wherein the resiliently compressible bellows is mounted between the barrels.

4. The integrated delivery device of claim 1, wherein the plunger bridge and the resiliently compressible bellows are operable with the same finger of one hand while being held in the same one hand.

5. The integrated delivery device of claim 1, wherein the liquid medicant comprises a cross-linkable polymer, and the syringe comprises a single barrel syringe containing a cross-linking initiator and/or a cross-linking accelerator that is retained on a porous media that is in fluid communication with said single barrel syringe.

6. The integrated delivery device of claim 5, wherein the cross-linkable polymer comprises an acrylic monomer.

7. A method of treating of the tissue comprising activating the integrated delivery device of claim 1 to deliver the powder medicant and the liquid medicant onto the tissue with no pre-mixing of the powder medicant and the liquid medicant to form a hemostatic or tissue sealing or coating on the tissue.

8. A method of claim 7, wherein the liquid medicant and the powder medicant are delivered within about 10 seconds of each other onto the tissue, and wherein the integrated delivery device is operated with one hand.

9. The method of claim 7, wherein said coating has a tissue interface side and an opposing top side; and wherein the powder medicant is directionally concentrated within the coating layer either at the tissue interface side or at the top side.

10. The method of claim 7, wherein said coating has a tissue interface side and an opposing top side; and wherein the powder medicant is distributed within the coating approximately uniformly as between the tissue interface side and the top side.

11. The method of claim 7, wherein the powder medicant comprises a bioabsorbable powder having at least one of hemostatic, wound treatment, fluid absorption, properties; the liquid medicant comprises a rapidly curable bioabsorbable liquid having hemostatic and or tissue sealing properties; and wherein said powder medicant is a non-curable powder material.

12. The method of claim 7, wherein said powder medicant is in the form of particles with an aspect ratio from about 1 to about 10, and an average particle size from about 90 microns to about 320 microns.

13. The method of claim 7, wherein said powder medicant is oxidized cellulose, oxidized regenerated cellulose, chitosan, starch, gelatin, collagen, or synthetic polymer.

14. The method of claim 7, wherein said powder medicant is oxidized regenerated cellulose.

15. The method of claim 7, wherein said liquid medicant comprises a fibrinogen and an initiator of fibrinogen conversion to fibrin.

16. The method of claim 7, wherein said liquid medicant comprises an acrylic monomer.

* * * * *